United States Patent [19]

Colombo et al.

[11] 4,203,735

[45] May 20, 1980

[54] PROCESS FOR PURIFYING GASEOUS FORMALDEHYDE

[75] Inventors: Paolo Colombo, Saronno; Pierino Radici, Turate, both of Italy

[73] Assignee: Societa' Italiana Resine S.I.R. S.p.A., Milan, Italy

[21] Appl. No.: 895,553

[22] Filed: Apr. 12, 1978

[30] Foreign Application Priority Data

Apr. 13, 1977 [IT] Italy .................. 22394 A/77

[51] Int. Cl.² .................... B01D 53/12
[52] U.S. Cl. ................... 55/26; 55/28; 55/34; 55/60; 55/62; 55/79
[58] Field of Search ........ 23/288 S; 55/28, 31, 55/33, 34, 60, 62, 68, 77, 78, 79, 181, 390, 26

[56] References Cited

U.S. PATENT DOCUMENTS

| | | | |
|---|---|---|---|
| 1,836,301 | 12/1931 | Bechthold | 55/79 X |
| 2,449,622 | 9/1948 | Roetheli | 23/288 S |
| 2,766,185 | 10/1956 | Pansing | 23/288 S X |
| 3,118,747 | 1/1964 | Codignola et al. | 55/33 |
| 3,177,631 | 4/1965 | Tamura | 55/34 X |
| 3,184,900 | 5/1965 | Codignola et al. | 55/33 X |
| 3,520,112 | 7/1970 | Mittelstrass et al. | 55/390 X |

*Primary Examiner*—Robert H. Spitzer
*Attorney, Agent, or Firm*—Sughrue, Rothwell, Mion, Zinn and Macpeak

[57] ABSTRACT

Raw gaseous formaldehyde is purified by passing it through a first series of superimposed fluidized beds of solid adsorbent, maintained at 80°–140° C., while continuously circulating solid adsorbent from each bed to the underlying bed and discharging from the lowermost bed the spent adsorbent, delivering the latter to the uppermost bed of a second series of superimposed fluidized beds of solid adsorbent, passing through the latter a stream of inert gas to strip the adsorbed formaldehyde at 130°–150° C., while continuously circulating said spent adsorbent from each bed to the underlying bed and discharging from the lowermost bed the adsorbent thus treated, delivering the latter to the uppermost bed of a third series of fluidized beds of solid adsorbent, and passing through the latter a stream of inert gas to regenerate the adsorbent at 145°–250° C., while continuously circulating the adsorbent from each bed to the underlying bed, discharging the regenerated adsorbent from the lowermost bed and recycling said regenerated adsorbent to the uppermost bed of the first series.

16 Claims, No Drawings

PROCESS FOR PURIFYING GASEOUS FORMALDEHYDE

The present invention relates to a continuous process for purifying raw gaseous formaldehyde to obtain formaldehyde monomer of high degree of purity, suitable for use in the production of its polymers and copolymers, or of its cyclic derivatives such as trioxane and tetroxan.

As is known in the art, raw gaseous formaldehyde can be produced by pyrolysis of its solid polymers, by using various methods, operating at a temperature of from 130° to 200° C. and usually in the presence of an inert liquid carrier. The solid material which is submitted to pyrolysis is preferably paraformaldehyde, having generally a content of formaldehyde higher than 80% by weight.

The raw gaseous formaldehyde thus obtained is similar in composition to the starting paraformaldehyde, when the pyrolysis reaction is carried out under controlled conditions. The impurities generally consist of water, methanol and formic acid, in addition to their mutual reaction products, products of reaction of said impurities with formaldehyde and products deriving directly from formaldehyde.

Several methods have been proposed in the art to purify formaldehyde. According to U.S. Pat. Nos. 3,118,747 and 3,184,900 the impurities present in raw formaldehyde are selectively adsorbed by means of solid adsorbents, inert with respect to formaldehyde.

The process of the present invention is also based on the use of solid adsorbents to purify raw formaldehyde. With respect to the known processes, it affords the production of pure formaldehyde with a very high purification efficiency.

Therefore, one object of the present invention is a continuous process for purifying raw formaldehyde by means of solid adsorbents, which affords the production of formaldehyde with a purity of at least 99.8%.

Another object of the present invention is a simple and convenient process for purifying raw formaldehyde, which affords a practically complete recovery of formaldehyde, in addition to a low consumption of the solid adsorbent.

A further object of the present invention is a process for purifying raw formaldehyde which affords a high purification efficiency, where by efficiency is meant the quantity of purified formaldehyde per unit of time and per unit of solid adsorbent used.

Thus, the invention provides a continuous process for purifying raw gaseous formaldehyde containing impurities comprising water, methyl alcohol, formic acid and mutual reaction products thereof, characterized by purifying said raw formaldehyde in an adsorption step by introducing a flow of said raw formaldehyde at the bottom of the lowermost bed of a first series of superimposed, spaced-apart, communicating fluidized beds of solid adsorbent, passing the flow of raw formaldehyde through said first series of fluidized beds and recovering purified formaldehyde at the top of the uppermost bed of said first series, maintaining the temperature within said first series of fluidized beds at a value of from 80° to 140° C., and continuously introducing solid absorbent into the uppermost bed of said first series, passing said solid adsorbent from each bed to the following one of said first series and continuously discharging from the lowermost bed of said first series exhausted solid absorbent containing adsorbed formaldehyde and impurities; selectively desorbing said adsorbed formaldehyde in a desorption step by stripping with an inert gas by continuously introducing said exhausted solid adsorbent into the uppermost bed of a second series of superimposed, spaced-apart, communicating fluidized beds of solid adsorbent, passing said exhausted solid adsorbent from each bed to the following one of said second series and continuously discharging the exhausted solid adsorbent thus treated from the lowermost bed of said second series, introducing at the bottom of the lowermost bed of said second series a stream of inert gas to strip said adsorbed formaldehyde and maintain fluidization conditions in said second series of fluidized beds, passing said stream of inert gas through the second series of fluidized beds and discharging from the top of the uppermost bed of said second series a stream of inert gas enriched in formaldehyde, and maintaining the temperature within said second series of fluidized beds at a value of from 130° to 150° C.; regenerating the exhausted solid adsorbent thus treated by stripping with an inert gas in a regeneration step by continuously introducing said exhausted solid adsorbent thus treated into the uppermost bed of a third series of superimposed, spaced-apart, communicating fluidized beds of solid adsorbent, passing said exhausted solid adsorbent thus treated from each bed to the following one of said third series and continuously discharging the thus regenerated solid adsorbent from the lowermost bed of said third series, introducing at the bottom of the lowermost bed of said third series a stream of inert gas to strip said adsorbed impurities and maintain fluidization conditions in said third series of fluidized bed, passing said stream of inert gas through the third series of fluidized beds and discharging from the top of the uppermost bed of said third series a stream of inert gas enriched in desorbed impurities, and maintaining the temperature within said third series of fluidized beds at a value higher than that maintained in the second series and from 145° to 250° C.; and continuously recycling the solid adsorbent thus regenerated to the uppermost bed of said first series.

According to a preferred embodiment the gaseous stream of inert gas enriched in desorbed formaldehyde, which is discharged from the desorption zone, is sent to the adsorption zone and preferably to the lowermost bed of said zone. When using this embodiment there is obtained a mixture of purified formaldehyde and inert gas. However, the presence of the inert gas does not affect the subsequent uses of the purified formaldehyde and the latter can easily be recovered from the said mixture.

By means of the process of the present invention the formaldehyde is freed from the impurities of protic polar character. As is known, these impurities are undesired, since they act as chain-transfer or chain-stopper agents during the polymerization of formaldehyde. Moreover, by operating according to the process of the present invention, the content of impurities having an aprotic polar character is reduced to very low values. As a result, high yields are obtained in the process for purifying formaldehyde and in the conversion of the purified formaldehyde into its polymers and copolymers.

When operating according to the process of the present invention a practically complete recovery of the formaldehyde is achieved.

Another advantage of the process of the present invention consists in the low consumption of solid adsorbent, owing to a better control of the temperature which results from the use of a multi-stage system.

Finally, by operating according to the process of the present invention, the purification efficiency, as previously defined, is very high and generally from 10 to 30 times higher than the values obtained when using fixed or mobile beds of solid adsorbent according to conventional methods.

This is probably due to the use of the particular multi-stage process of the invention and to the possibility of an efficient control of the temperature.

In particular, the very high heat-exchange coefficient obtained when operating according to the process of the invention permits a noticeable reduction of the exchange surfaces with respect to the known methods. As a result, the bulk of the apparatus can be noticeably reduced, while obtaining the same quantity of purified formaldehyde.

The solid adsorbents useful for the purposes of the present invention may be chosen from those described in the aforesaid U.S. Patents, and preferably from polylactic acid, polyphosphoric acid and sulphonated polystyrene or polyphenol resins. These products are preferably used in the form of their alkali and/or alkaline earth metal salts.

The weight ratio between the solid adsorbent and the raw formaldehyde to be purified essentially depends on the adsorbing power of the solid, in addition to the selected temperature and the amount of impurities present in the formaldehyde. The said weight ratio is preferably maintained at a value of from 2:1 to 5:1 at the adsorption step. It is obviously preferable to operate with low values of this ratio to better utilize the adsorbing capacity of the adsorbent, even if it is not convenient in practice to maintain the ratio at values near to the saturation value in order to avoid a slowing down of the adsorption kinetics.

The number of fluidized beds at each step mainly depends on the selected temperature, the characteristics of the solid adsorbent used, the content of impurities of the raw formaldehyde and on the content of residual impurities of the purified formaldehyde.

Thus, for example, when using a raw formaldehyde obtained by pyrolysis of paraformaldehyde, having a formaldehyde content of the order of 96% by weight, the number of fluidized beds is advantageously from 5 to 12 at the adsorption step, from 3 to 10 at the desorption step and from 5 to 15 at the regeneration step.

In each step the velocity of the gaseous stream assuring fluidization, as measured under the operating conditions and with an empty reactor, is generally from 0.1 to 1.0 meter/second and preferably from 0.2 to 0.6 meter/second, the selected value depending also on the grain size of the solid adsorbent. The height of each fluidized bed is generally from 5 to 100 cm, and preferably from about 20 to 50 cm. In practice, a weight ratio of about 1:1 is preferably maintained in the adsorption step between the inert gas and the adsorbed formaldehyde fed in. A weight ratio of about 1:2 may conveniently be maintained between the inert gas fed in at the desorption step and the inert gas fed in at the regeneration step.

The adsorption step is exothermal and the desorption and regeneration steps are endothermal. It is therefore necessary to control the temperature within each of the fluidized beds, generally by using heat-exchangers. The exchangers can be arranged within the fluidized bed or within the zone separating each bed from the next one.

The first solution is preferable, since it affords a higher purification efficiency.

The adsorption step is carried out at a temperature of from 80° to 140° C., the preferred range being from 110° to 125° C.

The spent solid adsorbent generally contains from 1 to 10% by weight of adsorbed formaldehyde and the latter is recovered at the desorption step, which is carried out at a temperature of from 130° to 150° C., the preferred values being from 135° to 145° C. It is generally preferable to maintain the desorption temperature at a value at least 10° C. higher than the adsorption temperature. The desorption is carried out by using an auxiliary gas inert towards formaldehyde, such as nitrogen.

The regeneration step is carried out by flowing an inert gas, such as nitrogen, in counter-current with the solid adsorbent and by operating at a temperature of from 145° to 250° C. The temperature is preferably from 150° to 180° C., the most suited temperature depending on the type of solid adsorbent. It is in fact necessary to operate below the decomposition temperature of the adsorbent. Preferably, the regeneration temperature is at least 15° C. higher than the desorption temperature.

Each step may be carried out in a tower. The solid adsorbent may be circulated from one bed to the bed located immediately below by means of internal or external pipings. In a particular embodiment the solid and the gas to be used in the different fluidized beds are passed through the holes of the foraminous plate located as the bottom of each fluidized bed. In another embodiment each fluidized bed is of the statistic or "piston-flow" type. To this end the plate located at the bottom of the fluidized bed is provided with suitable baffles.

In each case the distribution of the gaseous stream at the bottom of each individual fluidized bed must be as regular as possible, in order to obtain a uniform fluidization and to avoid attrition of the particles and the formation of non-homogeneous zones.

It is also important that the temperature be uniform. In particular, it is necessary to avoid the formation of cold zones in which formaldehyde is converted into its solid polymer. The temperature is easily controlled when using the multi-stage process of the invention.

EXAMPLE 1 (Comparative)

A stream of gaseous formaldehyde at 125° C., containing 4% by weight of water and 0.5% by weight of methanol, is fed at a rate of 1 kg/hour at the bottom of a column having an internal diameter of 3 inches, a height of 1.5 meters and an overall exchange surface of 1.61 $m^2$.

A ion-exchange macromolecular resin formed of sulphonated styrene-divinylbenzene copolymer in which the sulphonic groups are salified with sodium is introduced at the top of the column and circulated downwards through the column in counter-current with the gaseous stream at a rate of 3.5 kg/hour.

The resin, which has a grain size of from 0.4 to 1.0 mm, has been previously dried to a content of water lower than 0.05% by weight.

The adsorption being exothermal, the heat evolved is removed by means of exchangers operating at a wall temperature of 110° C. In the zone of maximum adsorption the temperature reaches under steady conditions a value of 135° C. Under the operation conditions the velocity of the gaseous stream is 0.055 m/second and the heat-exchange coefficient is 10 Kcal per m², per hour and per °C.

Analysis of the gaseous stream thus purified gives the following composition in weight percent:

| | |
|---|---|
| formaldehyde | >98% |
| methanol | 0.02–0.03% |
| water | 0.02–0.04% |
| by-products | <1.9% |

The by-products mainly consist of methyl formate, methylal and trioxan.

The solid adsorbent which is continuously discharged from the bottom of the column contains 5% by weight of adsorbed formaldehyde.

EXAMPLE 2

A gaseous stream of formaldehyde having the same composition and temperature as in Example 1 is continuously introduced at a rate of 2 kg/hour at the bottom of a column having an internal diameter of 50 mm and containing 10 fluidized beds. The salified resin of Example 1 is continuously fed at a rate of 7 kg/hour into the uppermost bed. The height of each bed under fluidization conditions is 20 cm, corresponding to 15 cm at rest. The passage of the resin from each bed to that immediately below is made by overflow.

The overall surface of the exchangers in contact with the gas, referred to the formaldehyde fed in, is identical with that used in Example 1. The wall temperature is 110° C. Under steady conditions and with a velocity of the gaseous stream of 0.35 m/second, the maximum adsorption temperature is 125° C. The heat exchange coefficient is higher than 200 Kcal per m², per hour and per °C.

Analysis of the gaseous stream thus purified shows the following composition in weight percent:

| | |
|---|---|
| formaldehyde | ≧99.8% |
| methanol | <0.02% |
| water | <0.02% |
| by-products | <0.2% |

The by-products mainly consist of methyl formate, methylal and trioxan.

The solid adsorbent which is continuously discharged from the bottom of the column contains 7% by weight of adsorbed formaldehyde.

EXAMPLE 3 (Comparative)

The resin which is discharged from the bottom of the mobile bed column of Example 1, is continuously introduced at the top of a similar column, at the bottom of which nitrogen is introduced at a hourly rate in kg equal to the percentage of formaldehyde adsorbed on the resin (5% by weight).

Desorption is carried out at a temperature of 142° C. by means of the mobile bed method. The gaseous stream discharged at the top of the column contains, in addition to nitrogen, 90% of the adsorbed formaldehyde.

The resin discharged from the bottom of the column contains 0.5% by weight of formaldehyde.

EXAMPLE 4

The resin discharged from the bottom of the adsorption column of Example 2 is continuously delivered to the uppermost bed of a column having an internal diameter of 50 mm and containing 8 fluidized beds. The height of each fluidized bed is 18 cm, corresponding to 13 cm at rest. The passage of the resin from each bed to that immediately below is made by overflow.

The column is operated at a temperature of 142° C. and fluidization is obtained by introducing nitrogen at the bottom of the column at an hourly rate in kg equal to the percentage of adsorbed formaldehyde (7% by weight). The maximum fluidization velocity in the column is 0.5 meter/sec.

Under these conditions the gaseous flow discharged from the top of the column contains, in addition to nitrogen 98.5% of the adsorbed formaldehyde and only trace amounts of the impurities.

The resin which is continuously discharged from the bottom of the column contains 0.105% by weight of formaldehyde.

EXAMPLE 5

The resin discharged from the bottom of the column of Example 4 is continuously delivered to the top of a column having the same mechanical characteristics as that of Example 2 and containing 7 fluidized beds.

The resin is regenerated at a temperature of 160° C., nitrogen being introduced at the bottom of the column at a rate of 1 kg/hour to maintain the resin under fluidization conditions. The maximum fluidization velocity is 0.4 meter/second.

The resin which is continuously discharged from the bottom of the column contains, under steady conditions, 0.02% by weight of water and is practically completely freed from methanol. The thus regenerated resin is delivered to the top of the adsorption column of Example 2.

We claim:

1. A continuous process for purifying raw gaseous formaldehyde containing impurities comprising water, methyl alcohol, formic acid and mutual reaction products thereof, which comprises purifying said raw formaldehyde in an adsorption step by introducing a flow of said raw formaldehyde at the bottom of the lowermost bed of a first series of superimposed, spaced-apart, communicating fluidized beds of solid adsorbent, passing the flow of raw formaldehyde through said first series of fluidized beds and recovering purified formaldehyde at the top of the uppermost bed of said first series, maintaining the temperature within said first series of fluidized beds at a value of from 80° to 140° C., and continuously introducing solid adsorbent into the uppermost bed of said first series, passing said solid adsorbent from each bed to the following one of said first series and continuously discharging from the lowermost bed of said first series exhausted solid adsorbent containing adsorbed formaldehyde and impurities; selectively desorbing said adsorbed formaldehyde in a desorption step by stripping with an inert gas, thereby recovering substantially all adsorbed formaldehyde, by continuously introducing said exhausted solid adsorbent into the uppermost bed of a second series of superimposed, spaced-apart, communicating fluidized beds of solid adsorbent, passing said exhausted solid adsorbent from each bed to the following one of said second series and continuously discharging the exhausted solid adsorbent thus treated from the lowermost bed of said second series, introducing at the bottom of the lowermost bed of said second series a stream of inert gas to strip said adsorbed formaldehyde and maintain fludization conditions in said second series of fluidized beds, passing said stream of inert gas through the second series of fluidized beds and discharging from the top of the uppermost bed of said second series a stream of inert gas enriched in desorbed formaldehyde, and maintaining the temperature within said second series of fluidized beds at a value of from 130° to 150° C.; regenerating the exhausted solid adsorbent thus treated by stripping with an inert gas in a regeneration step by continuously introducing said exhausted solid adsorbent thus treated into the uppermost bed of a third series of superimposed, spaced-apart, communicating fluidized beds of solid adsorbent, passing said exhausted solid adsorbent thus treated from each bed to the following one of said third series and continuously discharging the thus regenerated solid adsorbent from the lower most bed of said third series, introducing at the bottom of the lowermost bed of said third series a stream of inert gas to strip said adsorbed impurities and maintain fluidization conditions in said third series of fluidized bed, passing said stream of inert gas through the third series of fluidized beds and discharging from the top of the uppermost bed of said third series a stream of inert gas enriched in desorbed impurities, and maintaining the temperature within said third series of fluidized beds at a value higher than that maintained in the second series and from 145° to 250° C.; and continuously recycling the solid adsorbent thus regenerated to the uppermost bed of said first series.

2. The process of claim 1, in which said stream of inert gas enriched in desorbed formaldehyde is recycled to the adsorption step and combined with the stream of raw formaldehyde flowing through the first series of fluidized beds.

3. The process of claim 2, in which said stream of inert gas enriched in desorbed formaldehyde is introduced at the bottom of the lowermost bed of said first series.

4. The process of claim 1, wherein said solid adsorbent is selected from the group consisting of polylactic acid, polyphosphoric acid, sulfonated polystyrene and polyphenol resin and their alkali and/or alkaline earth metal salts.

5. The process of claim 1, in which said adsorption step is carried out by maintaining a weight ratio of from 2:1 to 5:1 between the solid adsorbent and the raw formaldehyde used.

6. The process of claim 1, wherein from 5 to 12 fluidized beds are used in said first series, from 3 to 10 in said second series and from 5 to 15 in said third series.

7. The process of claim 1, wherein the velocities of the gaseous streams flowing through the first, second and third series of fluidized beds are maintained at a value of from 0.1 to 1 meter/second.

8. The process of claim 7, wherein said velocities are maintained at a value of from 0.2 to 0.6 meters/second.

9. The process of claim 1, wherein the temperature maintained in the third series of fluidized beds is at least 15° C. higher than that maintained in the second series of fluidized beds.

10. The process of claim 1, wherein the height of the fluidized beds in said first, second and third series is from 5 to 100 cm.

11. The process of claim 1, wherein the temperature is maintained at a value of from 110° to 125° C. within said first series of fluidized beds, at a value of from 135° to 145° C. within said second series of fluidized beds and at a value of from 150° to 180° C. within said third series of fluidized beds.

12. The process of claim 1, wherein the control of the temperature within said first, second and third series of fluidized beds is obtained by means of heat-exchangers.

13. The process of claim 1, wherein nitrogen is used as stripping gas in said desorption step and regeneration step.

14. The process of claim 1, wherein the temperature in said first series of fluidized beds is 110°–125° C., the temperature in said second series of fluidized beds is 135°–145° C. and the temperature in said third series of fluidized beds is 150°–180° C.

15. The process of claim 14, wherein the temperature in said second series of fluidized beds is at least 10° C. higher than in the first series of fluidized beds and the temperature in said third series of fluidized beds is at least 15° C. higher than in said second series of fluidized beds.

16. The process of claim 14, wherein the temperature within each of said series of fluidized beds is maintained uniform.

* * * * *